(12) United States Patent
Scheiner et al.

(10) Patent No.: US 8,663,123 B2
(45) Date of Patent: Mar. 4, 2014

(54) APPARATUS AND METHOD FOR OUTPUTTING HEART SOUNDS

(71) Applicant: Cardiac Pacemakers, Inc., St. Paul, MN (US)

(72) Inventors: Avram Scheiner, Vadnais Heights, MN (US); Qingsheng Zhu, Wexford, PA (US); Arthur L. Olive, Stacy, MN (US); Don Villalta, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/928,674

(22) Filed: Jun. 27, 2013

(65) Prior Publication Data

US 2013/0289425 A1    Oct. 31, 2013

Related U.S. Application Data

(63) Continuation of application No. 13/456,795, filed on Apr. 26, 2012, now Pat. No. 8,478,391, which is a continuation of application No. 13/004,543, filed on Jan. 11, 2011, now Pat. No. 8,167,811, which is a continuation of application No. 11/037,276, filed on Jan. 18, 2005, now Pat. No. 7,883,470, which is a continuation of application No. 09/833,229, filed on Apr. 11, 2001, now Pat. No. 7,052,466.

(51) Int. Cl.
*A61B 5/025* (2006.01)

(52) U.S. Cl.
USPC ............................................ 600/528; 600/513

(58) Field of Classification Search
USPC ................................................ 600/528, 513
See application file for complete search history.

(56) References Cited

U.S. PATENT DOCUMENTS

| | | |
|---|---|---|
| 3,623,486 A | 11/1971 | Berkovits |
| 3,631,860 A | 1/1972 | Lopin |
| 3,738,369 A | 6/1973 | Adams et al. |
| 3,799,147 A | 3/1974 | Adolph et al. |
| 4,066,086 A | 1/1978 | Alferness et al. |
| 4,094,308 A | 6/1978 | Cormier |
| 4,208,008 A | 6/1980 | Smith |
| 4,289,141 A | 9/1981 | Cormier |
| 4,432,360 A | 2/1984 | Mumford et al. |
| 4,446,872 A | 5/1984 | Marsoner et al. |
| 4,548,204 A | 10/1985 | Groch et al. |
| 4,600,017 A | 7/1986 | Schroeppel |

(Continued)

OTHER PUBLICATIONS

"U.S. Appl. No. 09/833,229, Advisory Action mailed Jul. 2, 2004", 3 pgs.

(Continued)

*Primary Examiner* — Joseph Stoklosa
(74) *Attorney, Agent, or Firm* — Schwegman Lundberg & Woessner, P.A.

(57) ABSTRACT

An apparatus for outputting heart sounds includes an implantable system and an external system. The implantable system includes a sensor for generating sensed signals representing detected heart sounds, an interface circuit and a control circuit for receiving the sensed signals, generating data representing the heart sounds therefrom, and transmitting the data to the external system via the interface circuit. The external system includes an interface circuit for communicating with the implantable system, and a control circuit for receiving the data representing the heart sounds and for generating control signals that cause an output device to generate outputs representing the sounds. The implantable system may also include a sensor(s) for detecting cardiac electrical signals. In this case, outputs representing the cardiac electrical signals are also output.

20 Claims, 8 Drawing Sheets

(56) References Cited

U.S. PATENT DOCUMENTS

| | | |
|---|---|---|
| 4,628,939 A | 12/1986 | Little et al. |
| 4,649,930 A | 3/1987 | Groch et al. |
| 4,651,740 A | 3/1987 | Schroeppel |
| 4,721,114 A | 1/1988 | DuFault et al. |
| 4,763,646 A | 8/1988 | Lekholm |
| 4,793,361 A | 12/1988 | DuFault |
| 4,799,486 A | 1/1989 | DuFault |
| 4,799,493 A | 1/1989 | DuFault |
| 4,872,459 A | 10/1989 | Pless et al. |
| 4,905,706 A | 3/1990 | Duff et al. |
| 4,915,113 A | 4/1990 | Holman |
| 4,964,410 A | 10/1990 | Leahey et al. |
| 4,989,611 A | 2/1991 | Zanetti et al. |
| 5,012,815 A | 5/1991 | Bennett, Jr. et al. |
| 5,159,932 A | 11/1992 | Zanetti et al. |
| 5,247,945 A | 9/1993 | Heinze et al. |
| 5,271,392 A | 12/1993 | Ferek-Petric |
| 5,300,093 A | 4/1994 | Koestner et al. |
| 5,334,222 A | 8/1994 | Salo et al. |
| 5,365,932 A | 11/1994 | Greenhut |
| 5,427,112 A | 6/1995 | Noren et al. |
| 5,496,361 A | 3/1996 | Moberg et al. |
| 5,518,001 A | 5/1996 | Snell |
| 5,529,578 A | 6/1996 | Struble |
| 5,540,727 A | 7/1996 | Tockman et al. |
| 5,554,177 A | 9/1996 | Kieval et al. |
| 5,584,868 A | 12/1996 | Salo et al. |
| 5,607,460 A | 3/1997 | Kroll et al. |
| 5,674,256 A | 10/1997 | Carlson |
| 5,685,317 A | 11/1997 | Sjostrom |
| 5,687,738 A | 11/1997 | Shapiro et al. |
| 5,697,375 A | 12/1997 | Hickey |
| 5,700,283 A | 12/1997 | Salo |
| 5,716,382 A | 2/1998 | Snell |
| 5,725,559 A | 3/1998 | Alt et al. |
| 5,749,907 A | 5/1998 | Mann |
| 5,792,195 A | 8/1998 | Carlson et al. |
| 5,792,205 A | 8/1998 | Alt et al. |
| 5,836,987 A | 11/1998 | Baumann et al. |
| 5,843,142 A | 12/1998 | Sultan |
| 5,888,187 A | 3/1999 | Jaeger et al. |
| 5,899,928 A | 5/1999 | Sholder et al. |
| 5,921,938 A | 7/1999 | Aoyama et al. |
| 5,935,081 A | 8/1999 | Kadhiresan |
| 5,974,340 A | 10/1999 | Kadhiresan |
| 5,987,352 A | 11/1999 | Klein et al. |
| 5,991,661 A | 11/1999 | Park et al. |
| 6,006,132 A | 12/1999 | Tacker, Jr. et al. |
| 6,044,298 A | 3/2000 | Salo et al. |
| 6,044,299 A | 3/2000 | Nilsson |
| 6,045,513 A | 4/2000 | Stone et al. |
| 6,053,872 A | 4/2000 | Mohler |
| 6,058,329 A | 5/2000 | Salo et al. |
| 6,064,910 A | 5/2000 | Andersson et al. |
| 6,077,227 A | 6/2000 | Miesel et al. |
| 6,080,187 A | 6/2000 | Alt |
| 6,119,040 A | 9/2000 | Chirife |
| 6,139,505 A | 10/2000 | Murphy |
| 6,152,884 A | 11/2000 | Bjorgaas |
| 6,198,968 B1 | 3/2001 | Prutchi et al. |
| 6,254,544 B1 | 7/2001 | Hayashi |
| 6,256,536 B1 | 7/2001 | Kramer |
| 6,263,241 B1 | 7/2001 | Rosborough et al. |
| 6,264,611 B1 | 7/2001 | Ishikawa et al. |
| 6,295,365 B1 | 9/2001 | Ota |
| 6,298,267 B1 | 10/2001 | Rosborough et al. |
| 6,298,269 B1 | 10/2001 | Sweeney |
| 6,312,378 B1 | 11/2001 | Bardy |
| 6,366,811 B1 | 4/2002 | Carlson |
| 6,368,283 B1 | 4/2002 | Xu et al. |
| 6,409,675 B1 | 6/2002 | Turcott |
| 6,415,033 B1 | 7/2002 | Halleck et al. |
| 6,440,082 B1 | 8/2002 | Joo et al. |
| 6,453,201 B1 | 9/2002 | Daum et al. |
| 6,477,406 B1 | 11/2002 | Turcott |
| 6,527,729 B1 | 3/2003 | Turcott |
| 6,575,916 B2 | 6/2003 | Halleck et al. |
| 6,643,548 B1 | 11/2003 | Mai et al. |
| 6,650,940 B1 | 11/2003 | Zhu et al. |
| 6,665,564 B2 | 12/2003 | Lincoln et al. |
| 6,792,308 B2 | 9/2004 | Corbucci |
| 6,795,732 B2 | 9/2004 | Stadler et al. |
| 6,810,287 B2 | 10/2004 | Zhu et al. |
| 6,824,519 B2 | 11/2004 | Narimatsu et al. |
| 6,830,548 B2 | 12/2004 | Bonnet et al. |
| 6,845,263 B2 | 1/2005 | Kawaguchi |
| 7,052,466 B2 | 5/2006 | Scheiner et al. |
| 7,113,825 B2 | 9/2006 | Pastore et al. |
| 7,115,096 B2 | 10/2006 | Siejko et al. |
| 7,123,962 B2 | 10/2006 | Siejko et al. |
| 7,883,470 B2 | 2/2011 | Scheiner et al. |
| 8,167,811 B2 | 5/2012 | Scheiner et al. |
| 8,478,391 B2 | 7/2013 | Scheiner et al. |
| 2002/0001390 A1 | 1/2002 | Kawaguchi |
| 2002/0035337 A1 | 3/2002 | Oka |
| 2002/0082645 A1 | 6/2002 | Sweeney |
| 2002/0107450 A1 | 8/2002 | Ogura |
| 2002/0147401 A1 | 10/2002 | Oka |
| 2002/0151812 A1 | 10/2002 | Scheiner et al. |
| 2002/0151938 A1 | 10/2002 | Corbucci |
| 2003/0055352 A1 | 3/2003 | Hayek et al. |
| 2003/0069608 A1 | 4/2003 | Sweeney |
| 2003/0072458 A1 | 4/2003 | Halleck et al. |
| 2003/0093002 A1 | 5/2003 | Watrous et al. |
| 2003/0093003 A1 | 5/2003 | Watrous et al. |
| 2003/0120159 A1 | 6/2003 | Mohler |
| 2003/0176896 A1 | 9/2003 | Lincoln et al. |
| 2003/0208240 A1 | 11/2003 | Pastore et al. |
| 2003/0216620 A1 | 11/2003 | Jain et al. |
| 2003/0229289 A1 | 12/2003 | Mohler |
| 2004/0024423 A1 | 2/2004 | Lincoln et al. |
| 2004/0039419 A1 | 2/2004 | Stickney et al. |
| 2004/0039420 A1 | 2/2004 | Jayne et al. |
| 2004/0064056 A1 | 4/2004 | Ogura |
| 2004/0078059 A1 | 4/2004 | Ding et al. |
| 2004/0078060 A1 | 4/2004 | Ding et al. |
| 2004/0106960 A1 | 6/2004 | Siejko et al. |
| 2004/0106961 A1 | 6/2004 | Siejko et al. |
| 2004/0127792 A1 | 7/2004 | Siejko et al. |
| 2004/0138572 A1 | 7/2004 | Thiagarajan |
| 2004/0167417 A1 | 8/2004 | Schulhauser et al. |
| 2004/0215264 A1 | 10/2004 | Van Bentem |
| 2004/0225332 A1 | 11/2004 | Gebhardt et al. |
| 2004/0236239 A1 | 11/2004 | Murray et al. |
| 2004/0254481 A1 | 12/2004 | Brodnick |
| 2004/0267147 A1 | 12/2004 | Sullivan |
| 2004/0267148 A1 | 12/2004 | Arand et al. |
| 2005/0027323 A1 | 2/2005 | Mulligan et al. |
| 2005/0033190 A1 | 2/2005 | Bauer |
| 2005/0137490 A1 | 6/2005 | Scheiner et al. |
| 2006/0282000 A1 | 12/2006 | Zhang et al. |
| 2012/0209130 A1 | 8/2012 | Scheiner et al. |

OTHER PUBLICATIONS

"U.S. Appl. No. 09/833,229, Final Office Action mailed Mar. 26, 2004", 11 pgs.

"U.S. Appl. No. 09/833,229, Final Office Action mailed May 5, 2005", 7 pgs.

"U.S. Appl. No. 09/833,229, Non-Final Office Action mailed Oct. 19, 2004", 9 pgs.

"U.S. Appl. No. 09/833,229, Notice of Allowance mailed Nov. 10, 2005", 4 pgs.

"U.S. Appl. No. 09/833,229, Response filed Jan. 18, 2005 to Non-Final Office Action mailed Oct. 19, 2004", 14 pgs.

"U.S. Appl. No. 09/833,229, Response filed Jan. 29, 2004 to Non-Final Office Action mailed Oct. 29, 2003", 16 pgs.

"U.S. Appl. No. 09/833,229, Response filed Apr. 3, 2003 to Non-Final Office Action Mailed Nov. 20, 2002", 13 pgs.

"U.S. Appl. No. 09/833,229, Response filed May 25, 2004 to Final Office Action mailed Mar. 26, 2004", 14 pgs.

"U.S. Appl. No. 09/833,229, Response filed Jul. 23, 2004 to Advisory Action mailed Jul. 2, 2004 and Final Office Action mailed Mar. 26, 2004", 14 pgs.

(56) References Cited

OTHER PUBLICATIONS

"U.S. Appl. No. 09/833,229, Response filed Oct. 6, 2003 to Final Office Action mailed May 21, 2003", 15 pgs.

"U.S. Appl. No. 09/833,229, Advisory Action mailed Sep. 14, 2005", 3 pgs.

"U.S. Appl. No. 09/833,229, Final Office Action mailed May 21, 2003", 14 pgs.

"U.S. Appl. No. 09/833,229, Non-Final Office Action mailed Oct. 29, 2003", 12 pgs.

"U.S. Appl. No. 09/833,229, Non-Final Office Action mailed Nov. 20, 2002", 10 pgs.

"U.S. Appl. No. 09/833,229, Response filed Jun. 29, 2005 to Final Office Action mailed May 5, 2005", 12 pgs.

"U.S. Appl. No. 09/833,229, Response filed Sep. 29, 2005 to Advisory Action mailed Sep. 14, 2005", 10 pgs.

"U.S. Appl. No. 09/833,229, Response filed Oct. 7, 2002 to Restriction Requirement mailed Sep. 11, 2002", 1 pg.

"U.S. Appl. No. 09/833,229, Restriction Requirement mailed Sep. 11, 2002", 4 pgs.

"U.S. Appl. No. 11/037,276, Advisory Action mailed Oct. 29, 2008", 5 pgs.

"U.S. Appl. No. 11/037,276, Final Office Action mailed May 29, 2008", 7 pgs.

"U.S. Appl. No. 11/037,276, Final Office action mailed Aug. 19, 2008", 8 pgs.

"U.S. App. No. 11/037,276, Non-Final Office Action mailed Feb. 20, 2009", 8 pgs.

"U.S. Appl. No. 11/037,276, Non-Final Office action mailed Mar. 31, 2010", 4 pgs.

"U.S. Appl. No. 11/037,276, Non-Final Office Action mailed Aug. 21, 2009", 8 pgs.

"U.S. Appl. No. 11/037,276, Non-Final Office Action mailed Oct. 31, 2007", 6 pgs.

"U.S. Appl. No. 11/037,276, Notice of Allowance mailed Sep. 30, 2010", 6 pgs.

"U.S. Appl. No. 11/037,276, Preliminary Amendment mailed Sep. 29, 2005", 8 pgs.

"U.S. Appl. No. 11/037,276, Response filed Jan. 31, 2008 to Non-Final Office action mailed Oct. 31, 2007", 15 pgs.

"U.S. Appl. No. 11/037,276, Response filed May 20, 2009 to Non-Final Office Action mailed Feb. 20, 2009", 12 pgs.

"U.S. Appl. No. 11/037,276, Response filed Jun. 30, 2010 to Non-Final Office Action mailed Mar. 31, 2010", 8 pgs.

"U.S. Appl. No. 11/037,276, Response filed Jul. 28, 2008 to Final Office Action mailed May 29, 2008", 13 pgs.

"U.S. Appl. No. 11/037,276, Response filed Oct. 15, 2008 to Final Office Action mailed Aug. 19, 2008", 11 pgs.

"U.S. Appl. No. 11/037,276, Response filed Nov. 23, 2009 to Non-Final Office Action mailed Aug. 21, 2009", 13 pgs.

"U.S. Appl. No. 11/037,276, Response filed Dec. 19, 2008 to Final Office Action mailed Aug. 19, 2008 and Advisory Action mailed Oct. 29, 2008", 11 pgs.

"U.S. Appl. No. 13/004,543, Noitice of Allowance mailed Dec. 23, 2011", 7 pgs.

"U.S. Appl. No. 13/456,795, Non Final Office Action mailed Sep. 12, 2012", 7 pgs.

"U.S. Appl. No. 13/456,795, Notice of allowance mailed Mar. 5, 2013", 5 pgs.

"U.S. Appl. No. 13/456,795, Response filed Dec. 6, 2012 to Non Final Office Action mailed Sep. 12, 2012", 8 pgs.

"Guidant Prodsucts", [on-line]. [retrieved Nov. 24, 2000]. Retrieved from the Internet: <URL: http://ww.guidant.com/products/>, (Nov. 2000), 3 pgs.

US 8,663,123 B2

APPARATUS AND METHOD FOR OUTPUTTING HEART SOUNDS

CLAIM OF PRIORITY

This application is a continuation of application Ser. No. 13/456,795, filed on Apr. 26, 2012, which a continuation of application Ser. No. 13/004,543, filed on Jan. 11, 2011, now U.S. Pat. No. 8,167,811, which is a continuation of application Ser. No. 11/037,276, filed on Jan. 18, 2005, now U.S. Pat. No. 7,883,470, which is a continuation of application Ser. No. 09/833,229, filed on Apr. 11, 2001, now U.S. Pat. No. 7,052,466, the specifications of which are incorporated herein by reference in their entirety.

FIELD OF THE INVENTION

The present invention generally relates to the field of cardiac monitoring, and more particularly relates to detecting heart sounds using an implanted sensor, transmitting data indicative of the heart sounds to an external system, and outputting the heart sound data.

BACKGROUND

Cardiac pacemakers generally provide functions including sensing electrical signals generated by the heart, controlling stimulation of excitable tissues in the heart, sensing the response of the heart to such stimulation, and responding to inadequate or inappropriate stimulus or response (e.g., dysrhythmia) to deliver therapeutic stimuli to the heart. Some existing cardiac pacemakers also function to communicate with an external programmer device to support a variety of monitoring, diagnostic and configuration functions.

Certain cardiac pacemakers include an internal accelerometer for measuring the level of activity of the patient (e.g., movement caused by walking around, or by muscle twitches). Such pacemakers process (e.g., filter) the accelerometer signals to reduce noise interfering with the measurement of the patient's activity, such as the sounds generated by the heart itself, and then use the processed signals as inputs to algorithms for generating the signals used to control the stimulation of the heart. For example, if accelerometer signals indicate that a patient is walking briskly, the pacemaker may stimulate the heart to beat at a faster rate (often subject to an upper rate limit) than when the patient is at rest. While the accelerometer signal is used internally to control the heart rate, this signal is not transmitted by the pacemaker to an external programmer for subsequent display on a display device. Thus, the accelerometer signal itself is an internal signal which is not output to the user.

A common method of diagnosing heart problems involves comparing the electrical operation of the heart to its mechanical operation, and identifying electrical-mechanical disassociation. Typically, a physician listens to a patient's heart using a stethoscope placed on the surface of the patient's body, and compares the heart sounds to an electrocardiograph (ECG) trace generated by an ECG machine coupled to probes placed on the patient's chest. This method suffers from several disadvantages, including the need to use the stethoscope, the effect of various factors (e.g., the placement of the stethoscope, body fat, etc.) on the heart sounds, the need to electrically couple ECG probes to the patient's chest, the difficulties faced by the physician in accurately comparing the sounds heard using the stethoscope to the traces displayed by the ECG machine, and the relatively high level of skill needed to perform this comparison (especially if a physician is not available). This method also does not continuously monitor for electrical-mechanical disassociation, thus making it difficult to detect disassociation occurring between visits to the physician, and does not provide the ability to produce a written record showing a detected disassociation.

Thus, it would be desirable to provide a method and apparatus for outputting heart sounds, and/or for comparing electrical operation of the heart to mechanical operation of the heart, that overcome one or more of the above-described disadvantages.

SUMMARY OF THE INVENTION

According to one aspect of the invention, an implantable system includes a sensor for detecting heart sounds and generating sensed signals representative thereof, an interface circuit for communicating with an external system, and a control circuit coupled to the sensor and the interface circuit. The control circuit receives the sensed signals, generates data representative of the heart sounds therefrom, and transmits the data to the external system via the interface circuit. The sensor, interface circuit and control circuit are implantable. In another aspect, an implantable system also includes a second sensor for detecting cardiac electrical signals and generating second sensed signals representative thereof, and the control circuit also receives the second sensed signals, generates second data representative of the cardiac electrical signals therefrom, and transmits the second data to the external system. In another aspect, an implantable system also includes a third implantable sensor for detecting second cardiac electrical signals and generating third sensed signals representative thereof, and the control circuit receives the third sensed signals, generates third data representative of the second cardiac electrical signals therefrom, and transmits the third data to the external system.

According to another aspect, an external system includes an interface circuit to communicate with an implanted system, an output device, and a control circuit coupled to the interface circuit and output device. The control circuit receives data representing heart sounds detected by the implanted system, and generates control signals that, when applied to the output device, cause the output device to generate outputs which represent the heart sounds. In another aspect, a control circuit also receives data representing cardiac electrical signals from the implanted system, and generates control signals to cause the output device to generate outputs representing the heart sounds and cardiac electrical signals. In another aspect, a control circuit receives data representing second cardiac electrical signals from the implanted system, and causes the output device to generate outputs representing the heart sounds and the two cardiac electrical signals.

According to another aspect, a method of outputting heart sounds includes detecting heart sounds using an implanted sensor, and transmitting data representing the heart sounds to an external system. In another aspect, a method also includes detecting cardiac electrical signals using an implanted sensor and transmitting data representing the cardiac electrical signals to an external device. In another aspect, a method also includes detecting second cardiac electrical signals using an implanted sensor, and also transmitting data representing the second cardiac electrical signals to an external device.

According to another aspect, a method of outputting heart sounds includes receiving data representing heart sounds detected by an implanted system, generating control signals using the data, and applying the control signals to an output device to cause the output device to generate outputs which represent the heart sounds. In another aspect, a method also includes receiving second data representing cardiac electrical signals from the implanted system, and generating the control signals using the second data to cause the outputs generated by the output device to represent the cardiac signals. In another aspect, a method also includes receiving third data representing second cardiac electrical signals from the implanted system, and generating the control signals using the third data to cause the outputs to also represent the second cardiac signals.

Other aspects of the present invention will be apparent upon reading the following detailed description of the invention and viewing the drawings that form a part thereof.

DETAILED DESCRIPTION

In the following detailed description, reference is made to the accompanying drawings, which form a part hereof, and in which is shown by way of illustration specific embodiments in which the present invention may be practiced. These embodiments are described in sufficient detail to enable those skilled in the art to practice the present invention, and it is to be understood that the embodiments may be combined, or that other embodiments may be utilized and that structural, logical and electrical changes may be made without departing from the spirit and the scope of the present invention. The following detailed description is, therefore, not to be taken in a limiting sense, and the scope of the present invention is defined by the appended claims and their equivalents.

Figure 1:
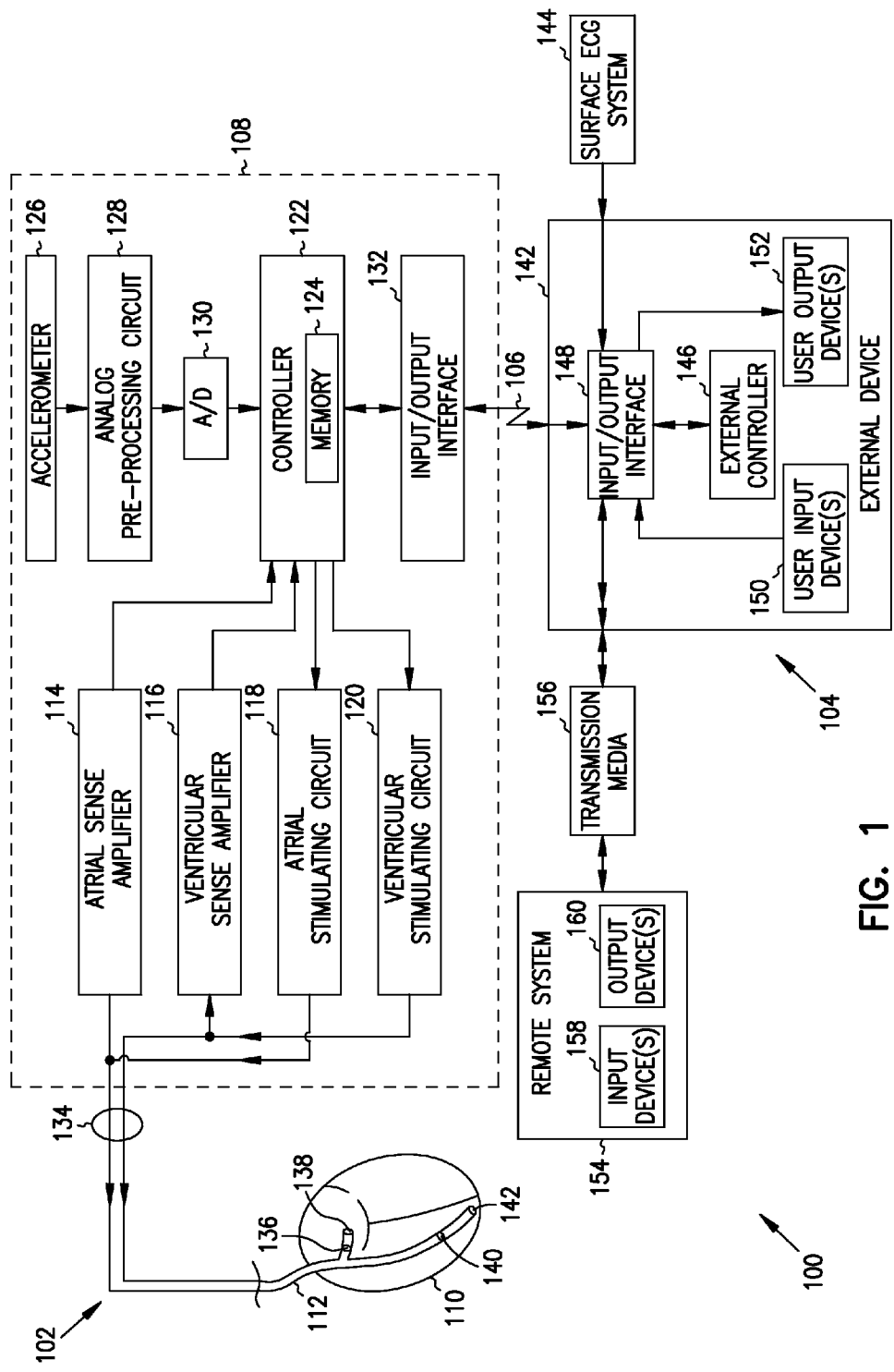
FIG. 1 is a block diagram of an exemplary system for detecting heart sounds using an implanted sensor, transmitting data representing the heart sounds to an external system, and outputting the heart sound data, according to one embodiment of the invention.

Referring to FIG. 1, an exemplary system 100 for outputting heart sounds in accordance with one embodiment of the present invention comprises an implantable system 102 and an external system 104. Implantable system 102 and external system 104 are configured to communicate via a communications link 106. In one embodiment, link 106 uses radio-frequency (RF) signals. In another embodiment, link 106 uses optical signals. These communications may support monitoring, diagnostic and configuration functions.

Implantable system 102 includes an implantable device 108 operatively coupled to a patient's heart 110 by a pacing lead 112. The components of implantable device 108 include an atrial sense amplifier 114, a ventricular sense amplifier 116, an atrial stimulating circuit 118, a ventricular stimulating circuit 120, a controller 122, a memory 124, an accelerometer 126, an analog pre-processing circuit 128, an analog-to-digital (A/D) converter 130, and an input/output (I/O) interface 132. The components of implantable device 108 are housed within an implantable housing (indicated by the broken lined box in FIG. 1.) which is implanted within the patient's chest cavity (e.g., in the pectoral region).

Atrial sense amplifier 114, ventricular sense amplifier 116, atrial stimulating circuit 118 and ventricular stimulating circuit 120 are operatively coupled to pacing lead 112 via a pair of conductors 134. Pacing lead 112 includes an atrial sensing electrode 136 and an atrial stimulating electrode 138 adapted to be disposed in the right atrial chamber of heart 110, and a ventricular sensing electrode 140 and a ventricular stimulating electrode 142 adapted to be disposed in the right ventricular chamber of heart 110. Sensed atrial and ventricular electrical signals generated by sensing electrodes 136 and 140 are applied to atrial and ventricular sense amplifiers 114 and 116, respectively, and atrial and ventricular stimulating signals generated by atrial and ventricular stimulating circuits 118 and 120 are applied to atrial and ventricular stimulating electrodes 138 and 142, respectively. Atrial sense amplifier 114, ventricular sense amplifier 116, atrial stimulating circuit 118, and ventricular stimulating circuit 120, are each also operatively coupled to controller 122.

In other embodiments, other sensing electrode configurations are used for internally sensing one or more electrical signals of heart 110. In one example, only one of sensing electrodes 136 and 140 is used. In another example, one or more electrodes placed within the body but outside of heart 110 are used for generating sensed cardiac electrical signals. In yet another example, a sensing electrode is placed within the implantable housing. In each of these examples, the sensing electrodes are operatively coupled to controller 122.

In the embodiment shown in FIG. 1, the sensing electrodes 136 and 140 and the stimulating electrodes 138 and 142 are disposed in the right side of heart 110. In other embodiments, one or more sensing electrode(s) and one or more stimulating electrode(s) are disposed in the left side of the heart (in lieu of being disposed in the right side of the heart, or in addition to sensing electrode(s) and stimulating electrode(s) disposed in the right side of the heart). The addition of left heart sensing may advantageously allow for the resolution of ambiguities due to disassociation of right and left heart conduction.

Controller 122 includes a micro-controller or microprocessor which is configured to execute a program stored in a read-only memory (ROM) portion of memory 124, and to read and write data to and from a random access memory (RAM) portion of memory 124. By executing the program stored in memory 124, controller 122 is configured to process the atrial and ventricular electrical signals from atrial and ventricular sense amplifiers 114 and 116, and to provide control signals to atrial and ventricular stimulating circuits 118 and 120. In response, stimulating circuits 118 and 120 provide stimulating pulses to heart 110 via atrial and ventricular stimulating electrodes 138 and 142 at appropriate times. In other embodiments, controller 122 may include other types of control logic elements or circuitry.

Implantable device 108 may be referred to as a dual-chamber pacemaker since pacemaking functions are provided to both atrial and ventricular chambers of heart 110. In another embodiment, the implantable system includes a single-chamber pacemaker that senses electrical signals and provides stimulating pulses to a single chamber of heart 110. In yet another embodiment, the implantable system does not provide any stimulation of heart tissues, but includes one or more sensing electrodes for sensing one or more electrical signals of heart 110, and for providing corresponding sensed signals to controller 122. In still another embodiment, the implantable system does not provide any sensing electrodes for sensing any cardiac electrical signals, but is configured to sense and transmit signals representing heart sounds using a sensor such as accelerometer 126, as described below.

In the remainder of this description, implantable device 108 is described as a dual-chamber pacemaker since the present system may be used with patients who have already had a pacemaker implanted in their bodies, thereby alleviating the need to implant a device solely for the purpose of monitoring heart sounds and/or intra-cardial electrical signals. It is to be understood, however, that implantable system 102 need not provide the stimulation functions described herein, and may provide other functions which are not described herein.

Accelerometer 126 is configured to provide sensed signals to analog pre-processing circuit 128, which generates an analog output signal which is digitized by A/D converter 130. The digitized accelerometer signal is received by controller 122. In the embodiment of FIG. 1, accelerometer 126 is located internally to the housing of implantable device 108. In another embodiment, accelerometer 126 is located externally to the implantable housing. Accelerometer 126 may include, for example, a piezo-electric crystal accelerometer sensor of the type used by pacemakers to sense the level of activity of the patient, or may include other types of accelerometers that are packaged to fit in the implantable housing. To detect heart sounds, other types of sound-detecting sensors or microphones may also be used, such as pressure sensors or vibration sensors configured to respond to sounds made by the heart.

In another embodiment, system 100 includes a plurality (two or more) of sound-detecting sensors. In this embodiment, the plurality of sensed heart sound signals from the plurality of sensors may be individually transmitted to external system 104 for display as individual traces, may be combined (e.g., averaged) by external system 104 before being displayed as a single trace, or may be combined by controller 122 before being transmitted to external system 104 as a single heart sound signal. These sensors may include different types of sensors, sensors that are located in different locations, or sensors that generate sensed signals which receive different forms of signal processing.

In one embodiment, accelerometer 126 is configured to generate sensed signals representative of two distinct physical parameters: (1) the level of activity of the patient; and (2) the heart sounds generated by heart 110. Accordingly, analog pre-processing circuit 128 is configured to pre-process the sensed signals from accelerometer 126 in a manner which conforms to the signal characteristics of both of these physical parameters. For example, if the frequencies of interest for measuring the patient's level of activity are below 10 Hz, while the frequencies of interest for detecting heart sounds are between 0.05 Hz and 50 Hz, then analog pre-processing circuit 128 may include a low-pass filter having a cutoff frequency of 50 Hz. Controller 122 may then perform additional filtering in software using, for example, a low-pass filter with a cutoff frequency of 10 Hz to detect the level of activity of the patient, and a band-pass filter with cutoff frequencies of 0.05 Hz and 50 Hz to detect the heart sounds, although these signal processing functions could also be performed by external system 104. Along with filtering, analog pre-processing circuit 128 may perform other processing functions including automatic gain control (AGC) functions.

In another embodiment, implantable device 108 has two pre-processing channels for receiving sensed signals from accelerometer 126. In still another embodiment, implantable device 108 includes two accelerometers, with one accelerometer configured to generate sensed signals representative of the level of activity of the patient and the other accelerometer configured to generate sensed signals representative of heart sounds. In these latter two embodiments, any hardware and/or software processing performed on the sensed signals can conform to the specific characteristics of the respective sensed signals. For example, the analog pre-processing circuit used for the level-of-activity sensed signals can provide a low-pass filter with a cutoff frequency of 10 Hz, while the analog pre-processing circuit for the heart-sound sensed signals can provide a band-pass filter with cutoff frequencies of 0.05 and 50 Hz. In the latter case, each accelerometer can be selected, located and/or oriented to maximize the detection of the respective physical parameter. In yet another embodiment, if the implantable device does not need to sense the level of activity of the patient, accelerometer 126 may measure only the sounds made by heart 110.

Controller 122 is capable of bi-directional communications with external system 104 via I/O interface 132. In one embodiment, I/O interface 132 communicates using RF signals. In other embodiments, I/O interface 132 communicates using optical signals, or a combination of RF and optical signals (e.g., RF signals for receiving data from external system 104 and optical signals for transmitting data to external system 104, or vice-versa). Controller 122 uses I/O interface 132 for bi-directional communications with external system 104 to support conventional monitoring, diagnostic and configuration pacemaker functions. Controller 122 also uses I/O interface 132 to telemeter data representative of the heart sounds sensed by accelerometer 126 to external system 104. In various embodiments, controller 122 further uses I/O interface 132 to telemeter data representative of cardiac electrical signals (i.e., electrogram or EGM signals), which may include data representative of atrial electrical signals (i.e., A EGM signals) sensed by atrial sensing electrode 136, and/or data representative of ventricular electrical signals (i.e., V EGM signals) sensed by ventricular sensing electrode 140. Thus, implantable system 102 is capable of sensing heart sounds, atrial electrical signals and ventricular electrical signals, and of telemetering data representative of the heart sounds and/or cardiac electrical signals to external system 104. In other embodiments, controller 122 telemeters data representative of cardiac electrical signals which were sensed by other configurations of internal cardiac sensing electrodes.

In one embodiment, external system 104 includes an external device 142 and a surface electrocardiograph (ECG) system 144. External device 142 includes an external controller 146, an I/O interface 148, user input device(s) 150, and user output device(s) 152. Using I/O interface 148, external controller 146 is configured for bi-directional communications with implantable device 108, for receiving input signals from input device(s) 150, and for applying control signals to output device(s) 152. Input device(s) 150 include at least one input device which allows a user (e.g., a physician, nurse, medical technician, etc.) to generate input signals to control the operation of external device 142, such as at least one user-actuatable switch, knob, keyboard, pointing device (e.g., mouse), touch-screen, voice-recognition circuit, etc. Output device(s) 152 include at least one display device (e.g., CRT, flat-panel display, etc.), audio device (e.g., speaker, headphone), or other output device which generates user-perceivable outputs (e.g., visual displays, sounds, etc.) in response to control signals. External controller 146 is configured to receive the data representative of heart sounds, atrial electrical signals and/or ventricular electrical signals from implantable system 102, and to generate control signals that, when applied to output device(s) 152, cause the output device(s) to generate outputs that are representative of the heart sounds, the atrial electrical signals and/or the ventricular electrical signals.

Surface ECG system 144 includes electrodes adapted to be electrically coupled to the surface of the patient's chest for sensing cardiac electrical signals, and is configured to produce ECG output signals which are coupled to I/O interface circuit 148. External controller 146 is configured to receive the ECG signals from I/O interface circuit 148, and to generate control signals which, when applied to output device(s) 152, cause the output device(s) to also generate outputs representative of the patient's ECG. Alternatively, in other embodiments, surface ECG electrodes are coupled directly to external device 142, rather than being supplied by a surface ECG system. In another embodiment, external device 142 does not receive surface ECG signals, and does not output such ECG signals. (Note: "ECG" is used herein to refer to cardiac electrical signals measured from the surface of the body, and "EGM" is used to refer to internally-measured cardiac electrical signals.)

In one embodiment, external device 142 comprises an external programming device for a cardiac pacemaker, such as the ZOOM™ external programmer available from the Guidant Corporation, except that the external programmer is configured (i.e., programmed or otherwise set up) to perform the various functions described in the present application.

In one embodiment, system 100 further includes a remote system 154 operatively coupled to communicate with external system 104 via transmission media 156. Remote system 154 includes one or more user input device(s) 158, and one or more user output device(s) 160, which allow a remote user to interact with remote system 154. Transmission media 156 includes, for example, a telephone line, electrical or optical cable, RF interface, satellite link, local area network (LAN), wide area network (WAN) such as the Internet, etc. Remote system 154 cooperates with external system 104 to allow a user located at a remote location to perform any of the diagnostic or monitoring functions that may be performed by a user located at external system 104. For example, data representative of heart sounds and/or cardiac electrical signals are communicated by external system 104 to remote system 154 via transmission media 156 to provide a visual display and/or an audio output on output device(s) 160, thereby allowing a physician at the remote location to aid in the diagnosis of a patient. System 154 is "remote" in the sense that a user of remote system 154 is not physically capable of actuating input device(s) 150 and/or of directly perceiving outputs generated by output device(s) 152. For example, system 154 may be located in another room, another floor, another building, another city or other geographic entity, across a body of water, at another altitude, etc., from external system 104.

Figure 2:
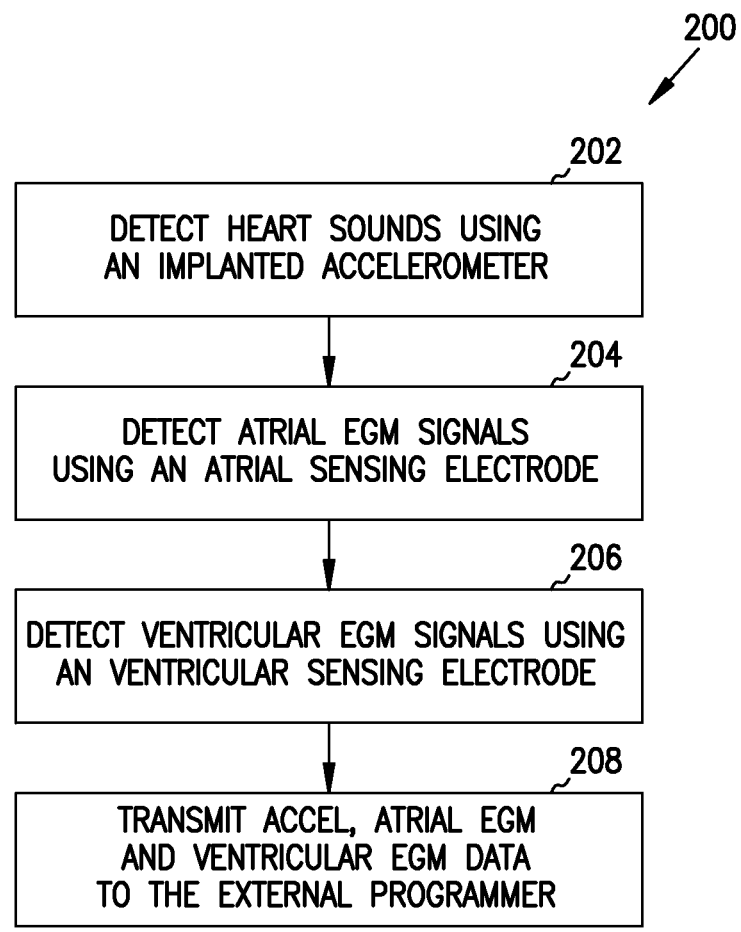
FIG. 2 is a flow chart illustrating one embodiment of the processing performed by the controller of the implantable device shown in FIG. 1.

Referring to FIG. 2, in one embodiment, the processing 200 performed by controller 122 of implantable device 108 includes detecting heart sounds by receiving sensed signals representative of the heart sounds from accelerometer 126 (at 202), detecting atrial electrical signals by receiving sensed signals representative of the atrial electrical signals from atrial sensing electrode 136 (at 204), detecting ventricular electrical signals by receiving sensed signals representative of the ventricular electrical signals from ventricular sensing electrode 140 (at 206), and transmitting data representative of the heart sounds, atrial electrical signals, and ventricular electrical signals to external device 142 (at 208).

In another embodiment, processing 200 further includes signal processing the accelerometer, atrial and ventricular sensed signals to generate processed sensed signals (between 206 and 208), and then transmitting the processed sensed signals to external device 142 (at 208). The signal processing may also be performed on only one or two of these sensed signals. However, performing the signal processing in implantable device 108 (rather than in external device 142, as described below relative to FIG. 3) may increase the computational requirements for implantable device 108, and may also increase the transmission load between devices 108 and 142. It is to be understood that the division of signal processing between implantable device 108 and external device 142 could be modified from that disclosed herein, as would be apparent to a person of skill in the art.

In another embodiment, processing 200 also includes storing one or more of the raw or processed sensed signals in memory 124 for later retrieval by external device 142. In still another embodiment, the processing performed by controller 122 does not include detecting the atrial electrical signals (at 204) and/or the ventricular electrical signals (at 206), in which case the corresponding EGM data is not transmitted to external device 142 (at 208). In yet another embodiment, the processing performed by controller 122 includes detecting other cardiac electrical signals sensed by other cardiac electrical signal sensors, and transmitting data representative of these other cardiac signals to external device 142.

Figure 3:
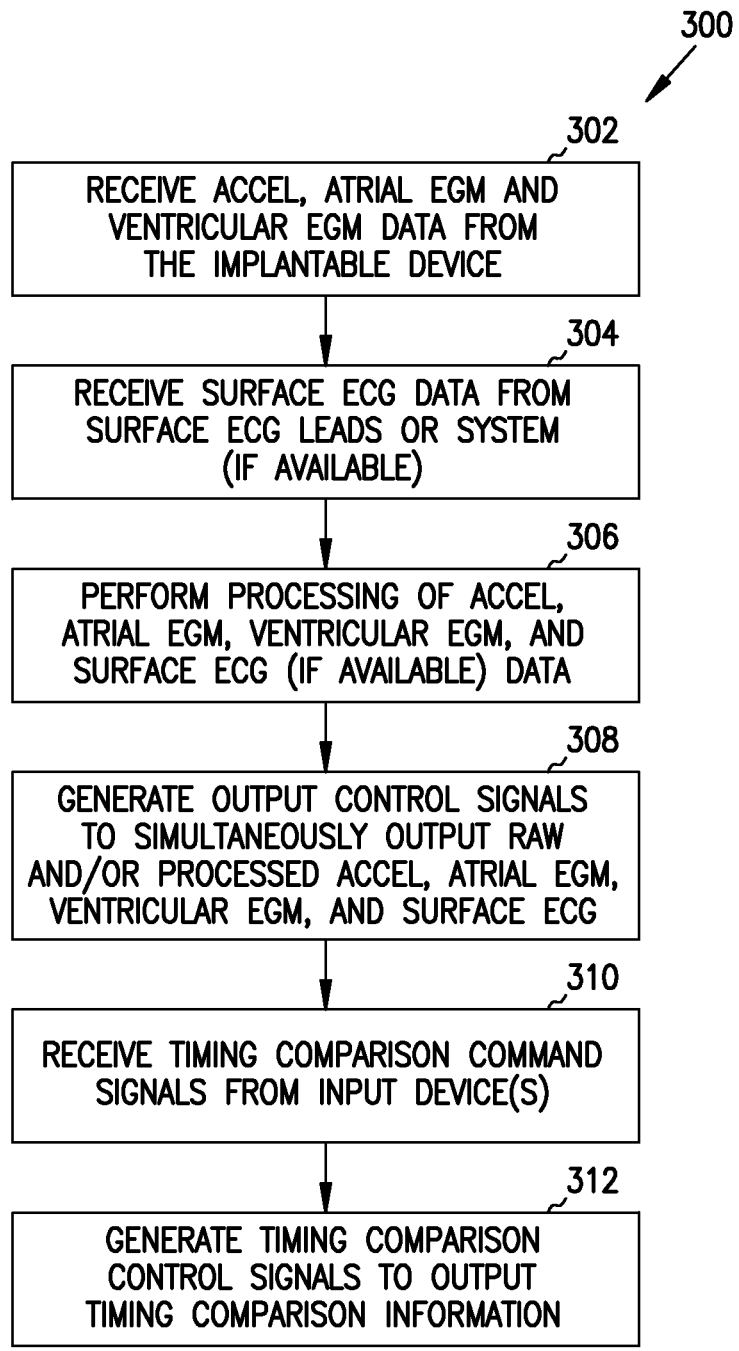
FIG. 3 is a flow chart illustrating one embodiment of the processing performed by the controller of the external device shown in FIG. 1.

Referring to FIG. 3, in one embodiment, the processing 300 performed by external controller 146 of external device 142 includes receiving the data representative of the heart sounds, atrial electrical signals and ventricular electrical signals from implantable device 108 (at 302), receiving surface ECG data from surface ECG system 144 or directly from surface ECG leads (at 304), processing the accelerometer, atrial electrical signals, ventricular electrical signals and surface ECG data (at 306), and generating output control signals to simultaneously output the raw and/or processed accelerometer, atrial electrical signals, ventricular electrical signals, and surface ECG signals on output device(s) 152 (at 308). Processing 300 may also include receiving timing comparison command signals from input device(s) 150 (at 310), and generating control signals to output timing comparison information on output device(s) 152 (at 312). Processing 300 may also include storing one or more of the raw or processed sensed signals in memory for later analysis.

In other embodiments, the processing performed by external controller 146 does not include receiving the atrial and/or ventricular electrical signals (at 302), or receiving surface ECG data (at 304), in which case the corresponding EGM data or surface ECG data is not processed (at 306) or output (at 308). Further, it is contemplated that external controller 146 may not perform any processing of the accelerometer, atrial electrical signals and/or ventricular electrical signals (at 306), and may instead receive corresponding processed data (rather than raw data) from implantable device 108. The processing of these signals (at 306) is illustrated in FIG. 3, however, to indicate that the processing described below in relation to FIG. 4 may well be performed by external device 142 rather than implantable device 108, thereby reducing the computational requirements for implantable device 108.

Figure 4:
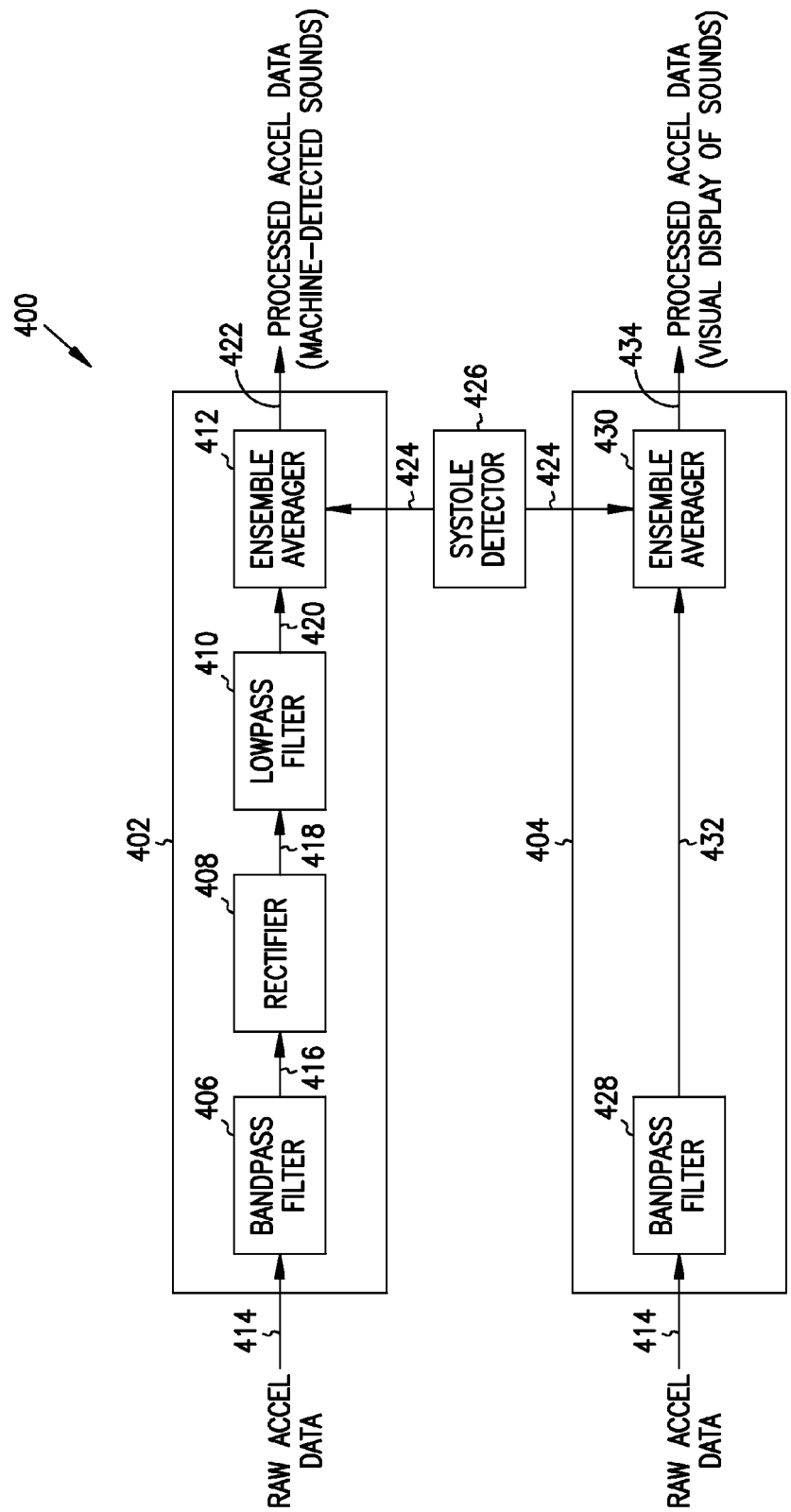
FIG. 4 is a block diagram illustrating one embodiment of the signal processing performed on the heart sound signals detected by the exemplary system shown in FIG. 1.

Referring to FIG. 4, the signal processing 400 performed on the heart sound data by external controller 146 in accordance with one embodiment of the invention is shown. In other embodiments, some or all of this signal processing could instead be performed by controller 122 of implantable device 108, or by either external or implantable hardware. Signal processing 400 includes a first processing path 402 used for machine detection of heart sounds, and a second processing path 404 used for visual display of heart sounds. Alternatively, only one of heart sound signal processing paths 402 and 404 is provided.

First processing path 402 includes a band-pass filter 406, a rectifier 408, a low-pass filter 410, and an ensemble averager 412, coupled in series. Raw accelerometer data 414 (representative of the heart sounds) is applied to band-pass filter 406, which has lower and upper cutoff frequencies set to pass frequencies indicative of heart sounds, to produce band-pass filtered data 416. In one example, the lower and upper cutoff frequencies are 0.05 Hz and 50 Hz, respectively. The cutoff frequencies are also set to reject frequencies due to movement of the patient (e.g., walking around, muscle twitches, etc.) to the extent that the heart sound signals still pass. Band-pass filtered data 416 is then applied to rectifier 408 to produce rectified data 418 that is, in turn, applied to low-pass filter 410 to produce filtered data 420. In one example, the cutoff frequency for low-pass filter 410 is 10 Hz.

Filtered data 420 is applied to ensemble averager 412 to produce processed accelerometer data 422, which is used for machine detection of heart sounds. Ensemble averager 412 is triggered by an output 424 of a systole detector 426, which is asserted to open a window of interest when the start of a cardiac cycle is detected based upon the electrical systole (which may be detected using the A EGM, V EGM and/or surface ECG signals). Ensemble averager 412 causes the repetitive heart sound data to be averaged over a number of cardiac cycles to accentuate the heart sounds (which are correlated to a particular frequency) while filtering out random or spurious noise (which are not correlated to a particular frequency). For example, ensemble averager 412 may average sequential heart sounds over a period of between 2 and 128 cardiac cycles, although other periods may also be used. In other embodiments, heart sounds are sequentially averaged over a period of time (e.g., one minute), or over the course of an event or condition (e.g., while the patient is performing an exercise), in which case only completed cardiac cycles will be averaged. Note that signal averaging the heart sound data includes the superposition and the summation of successive temporal samples of the pulsatile heart sound waveform.

Second processing path 404 includes a band-pass filter 428 and an ensemble averager 430, coupled in series. Raw accelerometer data 414 (representative of the heart sounds) is applied to band-pass filter 428, which has lower and upper cutoff frequencies set to pass frequencies indicative of heart sounds, to produce band-pass filtered data 432. In one example, the lower and upper cutoff frequencies are 0.05 Hz and 50 Hz, respectively. The cutoff frequencies are also set to reject frequencies due to patient movement to the extent that the heart sound signals still pass. Band-pass filtered data 432 is then applied to ensemble averager 430 to produce processed accelerometer data 434, which is used for visual display of heart sounds. Ensemble averager 430 is triggered by output 424 of systole detector 426, which is asserted to open a window of interest when the start of a cardiac cycle is detected based upon the electrical systole. Ensemble averager 430 causes the heart sound data to be averaged over a number of cardiac cycles (e.g., between 2 and 128 cardiac cycles, or other range) to accentuate the heart sounds while filtering out random or spurious noise. By eliminating the rectifier and low-pass filter of processing path 402, processing path 404 avoids eliminating information from the visual display of the heart sound data which may be useful to a physician, nurse, medical technician or other user of system 100.

In one embodiment, ensemble averager 430 includes logic to reject data from cardiac cycles outside the range of normal as such cycles may be of non-physiologic origin (e.g., PVC's). However, in the case of frequent PVC's, the PVC interval may become the norm. Thus, this logic may be adaptive so as to include such PVC's.

The signal processing for the heart sound data illustrated in FIG. 4 is merely exemplary, and other types of signal processing may be used. For example, the cutoff frequencies described above for the band-pass and low-pass filters may be varied, one or both of these filters may be eliminated, or other filters may be added. In one embodiment, the raw accelerometer data could be applied directly to an ensemble averager.

Figure 5:
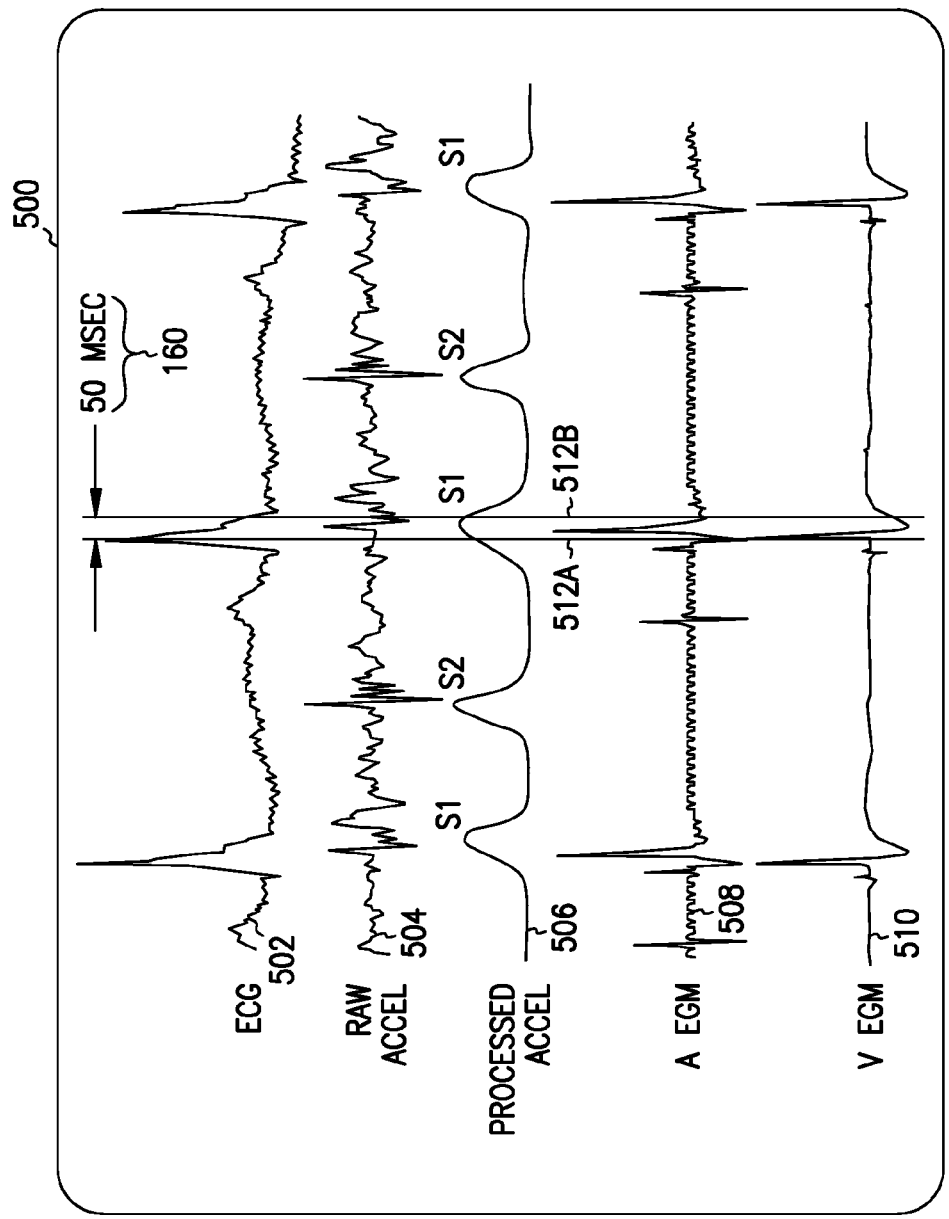
FIG. 5 is an exemplary output display screen that is generated by the external device shown in FIG. 1.

Referring to FIG. 5, an exemplary output screen display 500 generated by external device 142 on an output device 152 is shown. In this example, it is assumed implantable system 102 includes accelerometer 126, atrial sensing electrode 136, and ventricular sensing electrode 140, and that implantable system 102 transmits the raw sensed signals from each of these sensors to external device 142. It is also assumed that external device 142 generates display control signals that are output to a display to generate these outputs.

Output screen display 500 includes multiple horizontal traces, including a surface ECG trace 502, a raw accelerometer trace 504, a processed accelerometer trace 506, an atrial electrical signal ("A EGM") trace 508, and a ventricular electrical signal ("V EGM") trace 510. Alternatively, one or more of traces 502-510 may not be displayed. For example, since raw accelerometer trace 504 includes a relatively large amount of noise, this trace may not be displayed since it may not be easily interpreted by a user. Thus, display 500 simultaneously shows a visual trace of all five of these signals, which may be used by a user (e.g., a physician) to diagnose an electrical/mechanical disassociation of heart 110. Note that, if it is desirable for a user at a remote location to aid in the diagnosis of heart 110, the data representative of the heart sounds and electrical signals may be communicated by external device 142 to remote system 154 for display on one of output device(s) 160.

In one embodiment, display 500 includes one or more traces for displaying one or more cardiac electrical signals that were sensed from the left side of the heart, such as an "LV EGM" signal sensed by a sensing electrode disposed in the left ventricle.

In one embodiment, to help the user determine timing relationships between the signals shown in FIG. 5, external system 142 (and/or remote system 154) generates timing comparison control signals which, when applied to the display device, cause the display device to output timing comparison information indicating timing between the displayed signals. For example, system 142 (and/or system 154) may generate control signals which cause the display device to display a pair of vertical lines or calipers 512A and 512B, which can be moved horizontally by the user via a pair of input devices 150 (or input devices 158), with each input device controlling the position of one caliper. The calipers can help the user to compare timing between any of the displayed signals. To further aid the user, external system 142 (and/or remote system 154) may cause the display device to display a visual indicia 160 indicating the time period between the calipers. For example, indicia 160 indicates that the distance between calipers 512A and 512B represents 50 msec.

In one embodiment, to further aid the user in interpreting the display, heart sound data is automatically processed to identify one or more heart sounds, and visual indicia indicative of the identified sounds are also displayed on display 500. For example, external controller 146 may automatically process the sensed accelerometer data (e.g., processed accelerometer data 422) to detect the S1 and S2 heart sounds (and possibly the S3 heart sound), and to generate the display control signals so as to cause visual indicia (e.g., "S1" and "S2") to be displayed in association with the locations of the heart sounds on processed accelerometer trace 506 (or on raw accelerometer trace 504), as in FIG. 5. The S1 heart sound is associated with the closure of the AV valve and opening of the aortic valve in the heart, the S2 heart sound is associated with the subsequent closure of the aortic valve, and the S3 heart sound (less pronounced than the S1 and S2 sounds) is associated with the end of the heart's fast-filling phase during diastole. An exemplary method for automatically processing accelerometer signals to detect S1, S2 and S3 heart sounds is disclosed in U.S. Pat. No. 5,792,195, issued to Carlson et al. on Aug. 11, 1998, and incorporated by reference herein in its entirety. The heart sound indicia may help users to quickly and accurately identify these sounds, and may be especially helpful to less experienced users.

In one embodiment, to provide still additional aid to the user, the intra-cardiac EGM and/or surface ECG data may be automatically processed to identify one or more electrical cardiac events, and visual indicia indicative of the identified events may be displayed on display 500. For example, external controller 146 may be configured to automatically process the sensed atrial electrical data, ventricular electrical data, and/or surface ECG data to identify the P waves, QRS complexes, T waves, U waves, or other electrical cardiac events, and to generate the display control signals so as to cause visual indicia (e.g., "P", "QRS", "T", "U", etc.) to be displayed in association with the locations of the corresponding events on A EGM trace 508, V EGM trace 510, and/or surface ECG trace 502. The electrical cardiac event indicia may help users to quickly and accurately identify the electrical cardiac events, and may be especially helpful to less experienced users. External controller 146 may also provide additional processing (e.g., filtering) of the A EGM, V EGM and/or surface ECG signal to further delineate the events of interest (e.g., by low-pass filtering these signals to eliminate everything but the higher signal peaks).

To provide the user with additional operational control, the generation of the heart sound indicia and/or electrical cardiac event indicia on display 500 may be controlled by one or more of input devices 150 (or input devices 158). For example, a first input device (e.g., a switch) may be provided to allow the user to turn the heart sound indicia on or off, and a second input device may be provided to turn the electrical event indicia on or off.

In other embodiments, external device 142 performs additional processing to aid the user in interpreting display 500. For example, in one embodiment, external device 142 automatically calculates timing differences (e.g., electrical-to-mechanical time delay) for each heart beat, and outputs (e.g., lists, plots, etc.) the timing differences on a beat-to-beat basis. The user can examine the outputs to determine how the electrical-to-mechanical time delay changes over time (e.g., over a number of heart beats). In situations where electrical-to-mechanical disassociation occurs only in limited circumstances (e.g., when the patient is exercising), showing such timing differences over time may be useful to a physician.

In another embodiment, external controller 146 calculates and displays timing differences between automatically detected cardiac events, such as between automatically detected heart sounds, between automatically detected heart sounds and electrical cardiac events, between automatically detected electrical cardiac events, etc. For example, external controller 146 may calculate timing differences between the S1 and S2 heart sounds, between the QRS complex and S1 heart sound, or between the P wave and QRS complex, and then generate output control signals to cause visual indicia indicative of these timing differences (e.g., "n msec") to be displayed on display 500. In one embodiment, the timing differences that are displayed on display 500 are selected by the user based upon input signals generated by user input device(s) 150 (or input device(s) 158). In one example, a user employs a mouse to select a particular timing interval from a pull-down list of timing intervals that he or she would like to see calculated and displayed on display 500.

In one embodiment, one or more of output devices 152 (or output devices 160) comprises an audio device for generating audio outputs representative of the heart sounds. For example, raw accelerometer data 414 may be applied to a speaker to allow the user to hear and identify heart abnormalities. Alternatively, processed accelerometer data, such as processed accelerometer data 422 or 434, may be applied to an audio device to allow the user to hear and identify heart abnormalities. Other types of processed accelerometer data, including filtered and signal-averaged accelerometer data, may also be applied to an audio device to allow the user to hear and identify heart abnormalities. In each case, the user is presented with the heart sounds in the audio domain, which may more familiar to a physician or other user who is used to listening to heart sounds using a stethoscope. In each case, the user may also be presented with any or all of the traces shown in FIG. 5, such that the user may receive cardiac information in both the visual and the audio domains.

Figure 6:
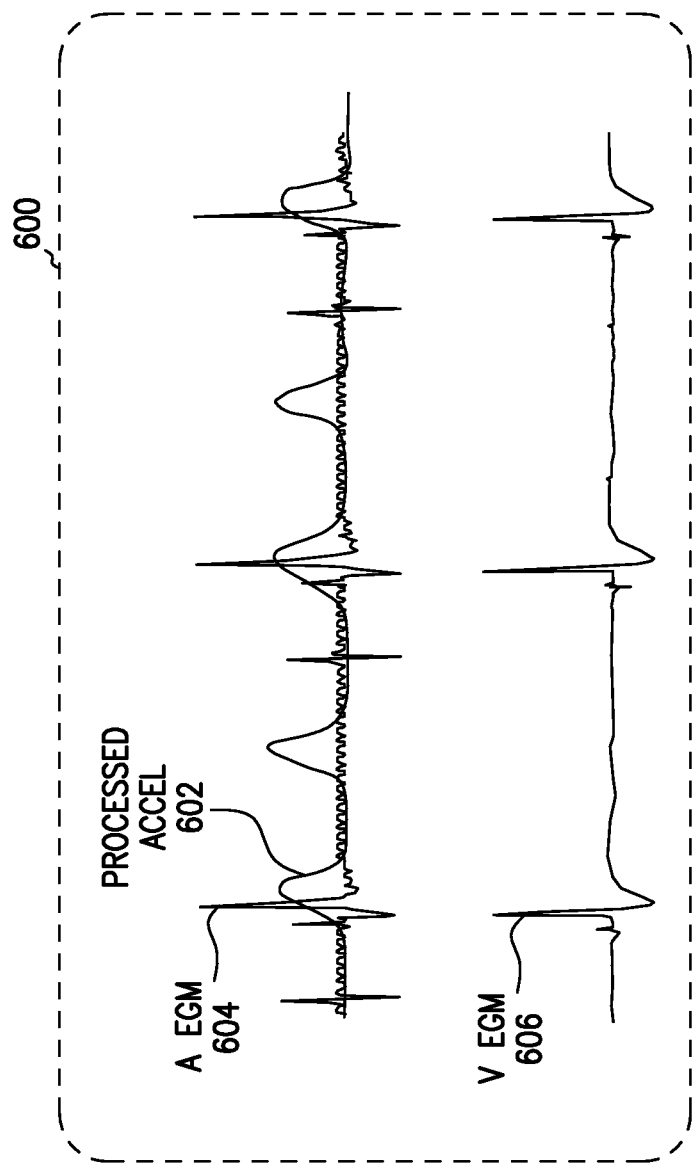
FIG. 6 is another exemplary output display screen that is generated by the external device shown in FIG. 1.

Referring to FIG. 6, another exemplary output screen display 600 generated by external device 142 on an output device 152 is shown. In this example, it is again assumed that implantable system 102 includes accelerometer 126, atrial sensing electrode 136, and ventricular sensing electrode 140, that implantable system 102 transmits the raw sensed signals from each of these sensors to external device 142, and that external device 142 generates display control signals that are output to a display to generate these outputs. The displayed traces include a processed accelerometer trace 602, an atrial electrical signal ("A EGM") trace 604, and a ventricular electrical signal ("V EGM") trace 606. Other traces, such as a surface ECG trace and/or a raw accelerometer trace, could also be displayed.

In this embodiment, to help the user determine timing relationships between the traces shown in FIG. 6, external device 142 (and/or remote system 154) is configured to generate timing comparison control signals which cause the display device to vertically move one or more of the traces under the control of the user via one or more of input devices 150 (or input devices 158). For example, each input device may control the vertical position of one trace. By vertically moving one or more of the traces, the user can superimpose the traces over one another to show timing comparisons. For example, as illustrated by the dashed lines in FIG. 6, the user has used an input device 150 to move A EGM trace 604 upward to superimpose this trace over processed accelerometer trace 602. By doing so, timing comparisons between traces 602 and 604 become readily apparent. Thus, in this embodiment, visual outputs of heart sounds may be superimposed over visual outputs of cardiac electrical signals to show timing comparisons therebetween. Note that, since display 600 does not indicate which superimposed signal was moved "over" another, superimposing trace A "over" trace B is the same as superimposing trace B "over" trace A.

Figure 7:
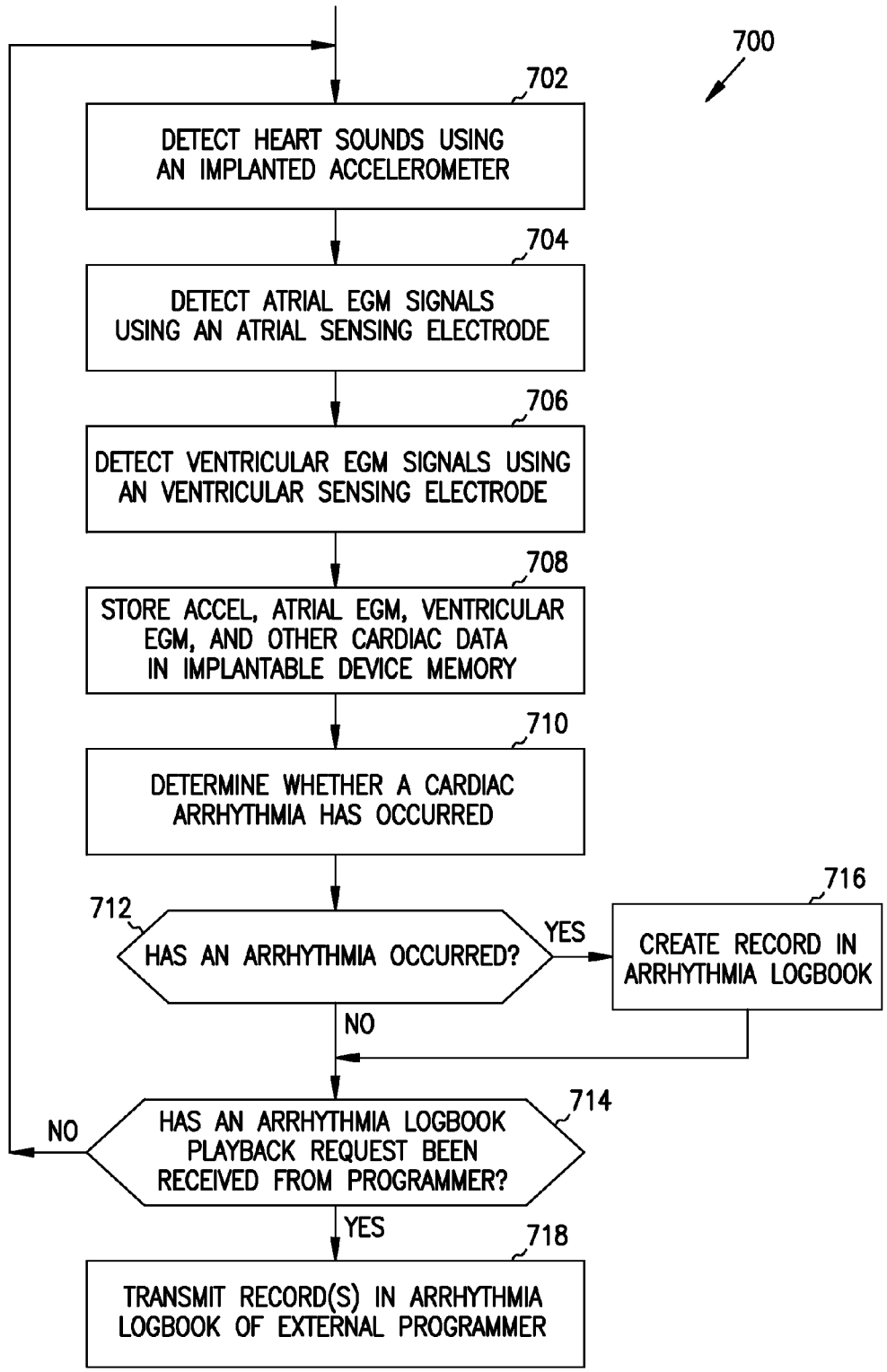
FIG. 7 is a flow chart showing another embodiment of the processing performed by the controller of the implantable device shown in FIG. 1, including a logbook feature.

Referring to FIG. 7, in another embodiment, implantable device 108 includes an arrhythmia logbook feature. With this feature, if an arrhythmia (e.g., an abnormally fast heart rate) is detected, implantable device 108 records data in memory for later examination by a physician for use in making a diagnosis. Implantable device 108 may, for example, continually record 10 seconds of data in an area of memory 124, and may simply rewrite over that area of memory. If, however, an arrhythmia is detected (e.g., the V EGM signal indicates that heart 110 is beating at an abnormally high rate of 180 beats/minute), the 10 seconds of recorded data is saved in another area of memory 124, along with an additional 20 seconds of data recorded after the arrhythmia. Other arrhythmia events may also be logged. Then, on the next visit of the patient to a doctor, the doctor can use external device 142 to read the data from the logbook, and can examine the data to look for arrhythmia events. For example, the logbook may indicate that, in the three months since the patient was last seen, heart 110 experienced five episodes of fast atrial heart beat, three atrial flutters, and one ventricular fibrillation. The data recorded by implantable device 108 in association with each arrhythmia event may include heart rate data, A EGM data, V EGM data and, in accordance with the present system, raw and/or processed heart sound data.

To provide the arrhythmia logbook feature, in one embodiment, controller 122 of implantable device 108 performs the processing 700 shown in FIG. 7. In particular, controller 122 detects heart sounds by receiving sensed signals representative of the heart sounds from accelerometer 126 (at 702), detects atrial electrical signals by receiving sensed signals representative of the atrial electrical signals from atrial sensing electrode 136 (at 704), detects ventricular electrical signals by receiving sensed signals representative of the ventricular electrical signals from ventricular sensing electrode 140 (at 706), and stores the accelerometer, atrial EGM and ventricular EGM data in memory 124 (at 708). In one embodiment, controller 122 continually stores 10 seconds of such data (along with other desired data, such as heart rate data) in a particular area of memory 124. If controller 122 determines that an arrhythmia has not occurred (at 712) and that no arrhythmia logbook playback request has been received from external device 142 (at 714), controller 122 loops back (to 702), and repeats these operations. As new data is collected and stored in memory 124, the oldest data is re-written by the new data such that the particular area of memory always stores the last 10 seconds of data. If an arrhythmia is detected (at 712), however, controller 122 creates a record in another area of memory (i.e., the arrhythmia logbook), and copies the last 10 seconds of data into that record. Then, for the next 20 seconds, controller 122 continues to monitor data, and stores this data within that same record. Thus, for each detected arrhythmia, controller 122 creates a record in memory 124 that contains data for the 10 seconds leading up to the arrhythmia, and the 20 seconds after the arrhythmia. In other embodiments, less than or more than this amount of data is stored either before or after each arrhythmia occurs. Then, when controller 122 determines that an arrhythmia logbook playback command is received from external device 142, controller 122 transmits the records from memory 124 to external device 142. External device 142 then outputs the data from these records to output device(s) 152 (or output device(s) 160). The physician can then examine the recorded data for each arrhythmia to aid in making a diagnosis. Thus, by using the arrhythmia logbook feature of the system, the physician is provided with heart sound information from both before and after the arrhythmia.

In one embodiment, system 100 may provide more sophisticated signal processing in cases of cardiac arrhythmia. For example, in the case of bigeminy, system 100 may be configured to use two averaging processes in order that like events are averaged separately. Exemplary signal processing techniques that could be employed by system 100 include, for example, those described in U.S. Pat. Nos. 4,799,493, 4,799,486, 4,793,361 and 4,721,114. In another embodiment, implantable device 108 may be configured to detect heart murmurs or extra heart sounds, to count such extra heart sounds, and to transmit such counts to external device 142 for output on one of output device(s) 150 (or devices 160).

Figure 8:
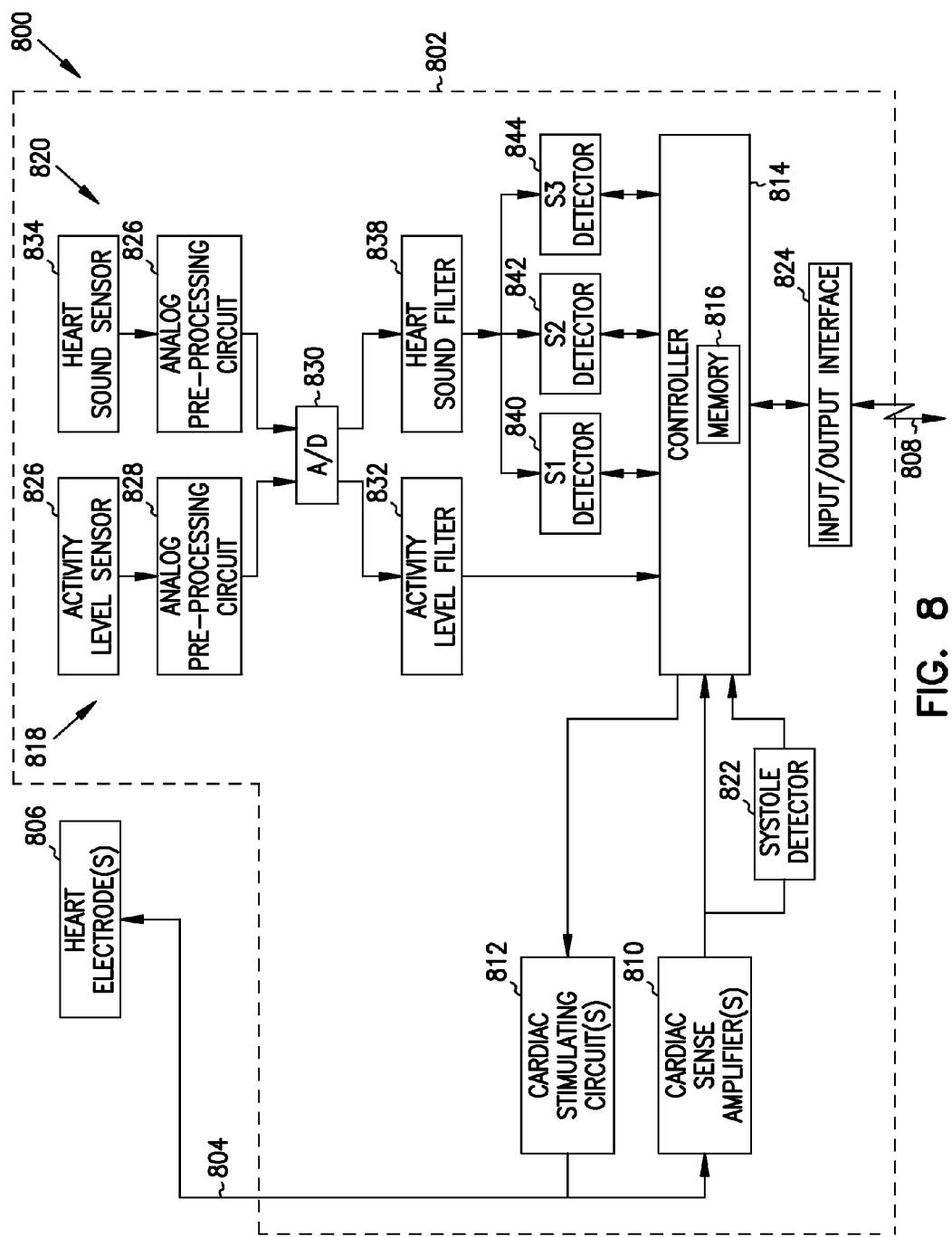
FIG. 8 is a block diagram of another exemplary system for outputting heart sounds.

Referring to FIG. 8, an exemplary system 800 for outputting heart sounds according to another embodiment comprises an implantable device 802 coupled to a patient's heart (not shown) by a pacing lead 804 and one or more heart electrode(s) 806, and operatively coupled to an external device (not shown) via a communications link 808. In one embodiment, heart electrode(s) 806 includes an atrial sensing electrode, ventricular sensing electrode, atrial stimulating electrode and ventricular stimulating electrode as in FIG. 1.

Implantable device 802 includes one or more cardiac sense amplifier(s) 810 and one or more cardiac stimulating circuit(s) 812 operatively coupled to heart electrode(s) 806 via lead 804. In another embodiment, where device 802 does not provide heart stimulation, device 802 does not include cardiac stimulating circuit(s) 812. Device 802 also includes a controller 814, a memory 816 operatively coupled to controller 814, an activity level detecting path 818, a heart sound detecting path 820, a systole detector 822, and an I/O interface 824. Activity level detecting path 818 includes an activity level sensor 826 for sensing patient activity, an analog pre-processing circuit 828 for pre-processing signals generated by activity level sensor 826, an A/D converter 830 for digitizing the activity level signals, and an activity level filter 832 for filtering the digitized signals to eliminate sources of noise such as those caused by heart sounds. Heart sound detecting path 820 includes a heart sound sensor 834 for sensing heart sounds, an analog pre-processing circuit 836 for pre-processing signals generated by heart sound sensor 834, A/D converter 830 for digitizing the heart sound signals (e.g., using a different channel than the channel used for the activity level signals), a heart sound filter 838 for filtering the digitized signals to eliminate sources of noise such as those caused by patient activity, an S1 heart sound detector 840 for detecting the S1 heart sound, an S2 heart sound detector 842 for detecting the S2 heart sound, and an S3 heart sound detector 844 for detecting the S3 heart sound. Controller 814 transmits data representing the patient's activity level and the S1, S2 and S3 heart sounds to the external device via I/O interface 824. Where S1, S2 and S3 heart sound detectors 840, 842 and 844 ensemble average the heart sound signals, controller 814 provides an output signal indicative of the start of a cardiac cycle from systole detector 822 to heart sound detectors 840, 842 and 844 for use as a trigger. In one embodiment, the outputs from S1, S2 and S3 heart sound detectors 840-844 comprise a sequence of pulses, each pulse representing a detected heart sound. The external device receives the heart sound and cardiac electrical signal data via link 808, and simultaneously outputs this data.

In one embodiment, activity level filter 832, heart sounds filter 838, heart sound detectors 840-844 and systole detector 822 are implemented by controller 814 through appropriate programming commands. In another embodiment, one or more of filters 832 and 838, and detectors 840-844, 822, are implemented by one or more hardware circuits. In another embodiment, some or all of the processing functions of FIG. 8 are performed by the external device instead of device 802. In another embodiment, system 800 includes S1 and S2 detectors 840 and 842, but does not include S3 detector 844. In another embodiment, system 800 includes other sound detectors for detecting other heart sounds. In another embodiment, when an electrical-mechanical disassociation is detected, stimulation timing provided by stimulating electrodes 138 and 142 is changed.

CONCLUSION

Thus, exemplary embodiments of an improved apparatus and method for outputting heart sounds, and/or for comparing electrical operation of the heart to mechanical operation of the heart, are disclosed herein. The disclosed apparatus and method for outputting heart sounds do not require the use of a stethoscope placed on the body of the patient, and are not subject to various factors which affect the heart sounds heard using a stethoscope. The disclosed apparatus and method for comparing electrical and mechanical operations of the heart also do not require the use of a stethoscope, are not subject to various factors which affect the heart sounds heard using a stethoscope, do not require ECG probes to be electrically coupled to the patient's chest, increase the accuracy of comparisons between heart sounds and electrical signals, decrease the level of skill needed to identify electrical-mechanical disassociation, provide for continuous monitoring of such electrical-mechanical disassociation, and are capable of producing a written record showing such disassociation.

As indicated above, the outputs generated by system 100 may be used by a physician to diagnose problems with heart 110 such as electrical-mechanical disassociation, or problems leading to cardiac arrhythmia. The outputs may also be used by a physician located remotely from the patient to diagnose the patient by checking the patient's heart sounds through a telephone, Internet or other communication connection. The sensed heart sound signals generated by system 100 may also be used for other purposes. For example, the heart sound signals may be useful in optimization of timing for CHF pacing, for determining the best AV delay, or for identifying the upper rate limit for a pacemaker.

Also, while the above description has focused on the relative timing of the various cardiac signals, the morphology or amplitude of the heart sound and cardiac electrical signals may also provide diagnostic information. For example, a heart sound signal with an amplitude lower than normal may be suggestive of certain heart abnormalities.

The above description is intended to be illustrative, and not restrictive. Many other embodiments will be apparent to those of ordinary skill in the art upon reviewing the present specification. For example, the implantable device described herein need not be a cardiac pacemaker, but may be another type of implantable device. Also, the external device described herein need not be an external pacemaker programmer, but may be another type of external device such as a cardiac monitor. The processing described herein as being performed by external controller 146 may also be performed by the implantable device, or by other combinations of hardware and software. Other signal processing routines may also be used. Further, while the system described herein outputs heart sounds, A EGM, V EGM and surface ECG signals, one or more of these signals need not be output, or may be replaced by the output of another internal or external cardiac signal. The scope of the present invention should therefore be determined with reference to the appended claims, along with the full scope of equivalents to which such claims are entitled.

What is claimed is:

1. A system for acquiring and processing first data representative of heart sounds of a patient and second data representative of cardiac electrical signals of the patient using an implantable device, comprising:

an external system configured to receive the first data and the second data from the implantable device via telemetry, the external system including:
   an interface circuit configured to communicate with the implantable device and to receive the first data and the second data from the implantable device;
   a disassociation detector circuit configured to detect electrical-mechanical disassociation using a comparison between the first data and the second data; and
   an output device configured to generate outputs representative of one or more of the heart sounds, the cardiac electrical signals, or the electrical-mechanical disassociation.

2. The system of claim 1, comprising a controller circuit configured to process the first data including detecting a plurality of heart sound components from the first data, and to process the second data including detecting a plurality of electrical cardiac events from the second data.

3. The system of claim 2, wherein the disassociation detector circuit is configured to calculate electrical-to-mechanical time delay for a plurality of heart beats, the electrical-to-mechanical time delay including timing difference between the plurality of heart sounds components from the first data and the plurality of electrical cardiac events from the second data.

4. The system of claim 3, wherein:
   the controller circuit is configured to detect a plurality of S1 heart sounds from the first data and to detect a plurality of QRS complexes from the second data; and
   the disassociation detector circuit is configured to calculate the electrical-to-mechanical time delay as the timing difference between the QRS complexes and the S1 heart sounds.

5. The system of claim 2, wherein the control circuit is configured to process the first data using a first processing path configured for machine detection of the heart sounds using the first data and a second processing path configured for presentation of the heart sounds.

6. The system of claim 1, comprising an accelerometer configured to sense the heart sounds of the patient.

7. The system of claim 1, comprising one or more electrodes configured to sense the cardiac electrical signals, the second data including at least one of an intra-cardiac electrogram or a surface electrocardiogram.

8. The system of claim 1, wherein the output device comprises a display device configured to generate visual outputs representative of the heart sounds and the cardiac electrical signals.

9. The system of claim 8, wherein the display device is configured to generate visual outputs representative of timing comparison between the heart sounds and the cardiac electrical signals, the timing comparison indicative of electrical-mechanical disassociation.

10. The system of claim 8, wherein the display device is configured to display one or more horizontally movable calipers for indicating time intervals between the heart sounds and the cardiac electrical signals.

11. A method, comprising:
   receiving first data representative of heart sounds and second data representative of cardiac electrical signals from an implantable device in a patient;
   processing the first data and the second data using an external system, the processing of the first data including using a first processing path configured for machine detection of the heart sounds using the first data and a second processing path configured for presentation of the heart sounds;

detecting electrical-mechanical disassociation using a comparison between the processed first data and the processed second data; and generating outputs representative of one or more of the heart sounds, the cardiac electrical signals, or the electrical-mechanical disassociation.

12. The method of claim 11, wherein:

processing the first data includes detecting a plurality of heart sounds components from the first data; and processing the second data includes detecting a plurality of electrical cardiac events from the second data.

13. The method of claim 12, wherein detecting the electrical-mechanical disassociation includes calculating electrical-to-mechanical time delay for a plurality of heart beats, the electrical-to-mechanical time delay including timing difference between the plurality of heart sounds components from the first data and the plurality of electrical cardiac events from the second data.

14. The method of claim 13, wherein:

detecting the plurality of heart sounds components includes detecting a plurality of S1 heart sounds from the first data;

detecting the plurality of electrical cardiac events includes detecting a plurality of QRS complexes from the second data; and calculating the electrical-to-mechanical time delay includes calculating time delay between the QRS complexes and the S1 heart sounds.

15. The method of claim 11, further comprising sensing the heart sounds using an implantable accelerometer.

16. The method of claim 11, wherein receiving the second data includes receiving data representative of an intra-cardiac electrogram.

17. The method of claim 11, wherein receiving the second data includes receiving data representative of a surface electrocardiograph signal.

18. The method of claim 11, wherein generating the outputs includes generating visual outputs representative of one or more of the heart sounds, the cardiac electrical signals, or the electrical-mechanical disassociation.

19. The method of claim 18, wherein generating the visual outputs representative of electrical-mechanical disassociation includes generating timing comparison between the heart sounds and the cardiac electrical signals.

20. The method of claim 18, wherein generating the visual outputs representative of electrical-mechanical disassociation includes displaying one or more horizontally movable calipers for indicating time intervals between the heart sounds and the cardiac electrical signals.

* * * * *